US005098598A

United States Patent [19]

Sankey et al.

[11] Patent Number: 5,098,598

[45] Date of Patent: Mar. 24, 1992

[54] PERCARBOXYLIC ACIDS

[75] Inventors: John P. Sankey, Warrington; Alun P. James, Liverpool; Inderbir K. Tranter, Warrington, all of England; Joseph M. Schofield, Paris, France

[73] Assignee: Interox Chemicals Limited, London, England

[21] Appl. No.: 453,278

[22] Filed: Dec. 22, 1989

[30] Foreign Application Priority Data

Dec. 24, 1988 [GB] United Kingdom ................ 8830235

[51] Int. Cl.[5] ..................... C01B 15/10; C07C 409/00

[52] U.S. Cl. .......................... 252/186.42; 252/186.26; 252/95; 562/2

[58] Field of Search ........................ 252/186.42; 562/2

[56] References Cited

U.S. PATENT DOCUMENTS 2,813,896 11/1957 Krimm .................................. 562/2
3,928,223 12/1975 Murray .......................... 252/186.42
4,634,551 1/1987 Burns et al. ............................ 562/2
4,852,989 8/1989 Burns et al. .................... 252/186.42

*Primary Examiner*—Robert L. Stoll
*Assistant Examiner*—Joseph D. Anthony
*Attorney, Agent, or Firm*—Larson and Taylor

[57] ABSTRACT

The incorporation of many percarboxylic acids in household formulations is precluded from by adverse physicochemical properties, such as a propensity to decompose too quickly during storage or explode on impact or when subjected to pressure, though otherwise they would be effective disinfectants and bleaching agents, especially at hand-hot temperatures.

The invention provides a stable and effective selection of organic percarboxylic acids which satisfy one or other of the general formulae (1) or (2):

$$R^a—CO—NH—C_6H_4—CO—OOH \quad (1)$$

or $$HOO—CO—R^b—CO—NH—C_6H_4X \quad (2)$$

in which in formula (1) the amido substituent is meta or para to the percarboxylic acid group and $R^a$ represents an alkyl group containing from 1 to 5 carbons in formula (1) and in formula (2) $R^b$ represents a branched or preferably linear alkylene group containing from 4 to 7 carbon atoms of which at least 4 are linear and X represents hydrogen or a substituent like chloride. In particularly preferred peracids satisfying formula (1), $R^a$ represents an ethyl or n-propyl or n-butyl group para to the percarboxylic acid substituent and in those satisfying formula (2), $R^b$ represents a linear tetra- or penta-methylene group.

The invention also provides bleaching, washing and disinfecting compositions containing such peracids and processes using them for such purposes.

5 Claims, No Drawings

PERCARBOXYLIC ACIDS

The present invention relates to percarboxylic acids and more particularly to percarboxylic acids which contain within their structure an amido linkage, to the preparation of such percarboxylic acids and to their use in bleaching compositions and in washing compositions.

Organic percarboxylic acids, strictly peroxycarboxylic acids, which alternatively are sometimes called organic peracids, as a class, are potentially very useful oxidising agents as a result of their high electropotential which enables them to bleach very effectively a wide range of stains that mark domestic laundry or non-absorbent surfaces in the home and very useful disinfectants or sanitizers on account of their biocidal activity against a broad spectrum of pathogenic micro-organisms. Self-evidently, some percarboxylic acids are more effective than others in such activities, but the relative efficacy of the percompounds is only one key factor in determining the potential usefullness of such percompounds because they vary also in a second key area, which is the physical characteristics of the percompounds and specifically their sensitivity to impact, pressure or thermal shock and their propensity to decompose during storage, either by themselves or in contact with other components of washing or bleaching compositions. Variation in respect of both factors occurs as a direct result of what else is present in the percarboxylic acid molecule and the structural relationship of for example the miscellaneous substituents to the percarboxylic acid group and to each other.

It is very easy for the skilled person in this field to set out his criteria for a most acceptable peroxyacid, namely effective washing and bleaching performance whilst offering sufficient resistance to impact, pressure and thermal shocks and a long shelf-storage life, i.e. successful, safe and stable, but it is not at all easy to predict from the formula alone the extent to which many sub-classes of peroxyacid attain those criteria, despite the impression fostered by the presence of general formulae for peracids in many patent specifications, e.g. U.S. Pat. No. 4,259,201 of HO—O—(CO)—R—Y which appear to equate aliphatic and aromatic peroxyacids and a wide range of substituents. None the less, as the present investigations into the preparation of a wide range of peroxyacids and their properties progressed, the present investigators became aware of certain correlations within any given sub-class of peroxyacids.

One of the sub-classes of peroxyacids investigated comprised those containing within their structure an amide link. General formulae for such compounds, $$R^1—CO—N(R^5)—R^2—CO—OOH$$

and $$R^1—N(R^5)—CO—R^2—CO—OOH$$

have been given by M. E. Burns et al in U.S. Pat. No. 4,634,551, by M. E. Burns in U.S. Pat. No. 4,686,063, both assigned to The Procter & Gamble Company and also in EP-A-0 170 386 in the name of the same assignee. The patentees offer quite a wide range of alternatives for the components. $R^1$ can be alkyl, aryl or alkaryl containing 1 to 14 C atoms, $R^2$ can likewise be alkylene, arylene or alkarylene containing 1 to 14 C atoms, and $R^5$ can be hydrogen or alkyl, aryl or alkaryl containing 1 to 10 C atoms. The components can contain branching and substitution alkyl, aryl halogen, nitrogen, sulphur and other typical substituent groups of organic compounds. The texts generalise about the properties of the peroxyacids and assert that they enjoy excellent bleaching performance, and improved, surprisingly good, thermal stability though acknowledging the need for an exotherm control agent to be employed.

The generalised descriptions and the claims in these patent specifications were based upon a number of Examples, but these related to completely aliphatic compounds or the generation of the peroxyacid in situ except for Example VI of U.S. Pat. No. 4,634,551. Example IX of the same patent generates a peroxyacid in situ in solution, but does not isolate and store the peroxyacid as a solid isolate. These peroxyacids were made and tested during the course of the programme of research which resulted in the present invention. It was found that neither peroxyacid exhibited an acceptable combination of properties and indeed both were inferior to the aliphatic peroxyacids with which they had been linked. They were found by the instant inventors to suffer from either poor bleach performance or poor physical properties. Such poor results explain why Burns chooses only to make his peroxyacid in Example IX in situ and chooses not to describe the results obtained using his peroxyacid of Example VI they would contrast unfavourably with results given from his aliphatic peroxyacids and introduce great doubt as to whether the breadth of claim was appropriately drawn and fairly based.

The present investigation of a large number of peroxyacids containing both an amide link and an arylene group has revealed substantial variation in the properties of the compounds, both as regards effectiveness and stability/hazardness. Moreover, a similar change such as increasing chain length in a substituent was shown to result in different effects, depending on the remainder of the molecule, for example improving thermal stability for one sub-set of peroxyacids, but impairing thermal stability for a second subset.

It is an object of the present invention to define a set of peroxyacid compounds containing both an amide link and an aromatic group which simultaneously offer acceptable bleaching/washing performance and acceptable physical properties.

According to the present invention there is provided an organic peroxyacid which satisfies one or other of the general formulae (1) or (2):

$$R^a—CO—NH—C_6H_4—CO—OOH \quad (1)$$

or $$HOO—CO—R^b—CO—NH—C_6H_4—X \quad (2)$$

in which in formula (1) the amido substituent is meta or para to the percarboxylic acid group and $R^a$ represents an alkyl group containing from 1 to 5 carbons in formula (1) and in formula (2) $R^b$ represents a linear or branched alkylene group containing from 4 to 7 carbon atoms of which at least 4 are linear and X represents hydrogen or a compatible non-released substituent.

It will be recognised that the peroxyacids of the present invention share the feature of the aromatic nucleus being substituted by the nitrogen atom of the amide linkage instead of by the carbonyl carbon in the amide linkage. This seems to be one requirement for obtaining a peroxyacid containing an amido aromatic group that offers acceptable washing and stability properties, but attainment of that requirement by itself appears not to be sufficient. In addition, it appears to be of practical importance to choose a complementary alkyl/alkylene group containing an appropriate number of carbon atoms. In the case of peroxyacids obeying formula (1), this means choosing an alkyl group that is not too large, because the thermal stability becomes worse as the size of the alkyl group increases. On the other hand, in the case of peroxyacids obeying formula (2), this means choosing an alkylene group that is not too short, because the shorter ones are decreasingly stable. In any event, it will be recognised that stability is not predicated simply by the molecular weight of the compound, but must also take into account its spacial structure. This point is confirmed by the way in which the respective stability of the two structures change in response to an increase in their molecular weight, as indicated hereinabove.

In general formula (1), $R^a$ is especially suitably para to the peroxycarboxylic acid substituent. It is preferably linear. Advantageously, it contains at least 2 carbon atoms and particularly preferably represents an ethyl, propyl or butyl group, because the resultant peroxyacid attains very good washing performance, has at least good thermal stability and does not suffer from sensitivity to impact. Each of the three resultant peroxyacids enjoys a particular advantage relative to the others. That containing ethyl as $R^a$ has excellent thermal stability, the best of the three, but a response in the standard pressure time test for potential explosiveness that is little better than that achieved by a vogue peroxyacid at present, diperoxydodecanedioc acid (DPDDA). That containing butyl is shown by the pressure time test to be totally unresponsive, i.e. the most resistant to explosion, but as indicated previously, its thermal stability is not quite as good as the three most stable alkaneamidoperoxybenzoic acids. That containing propyl is shown by the tests to marry a thermal stability that is better than that of butyl with a response in the pressure-time test that is better than that of ethyl and thus represents an excellent compromise.

$R^a$ in the general formula (1) also includes methyl and pentyl. Whilst both are useable, the former advantageously benefits from desensitisation with an effective amount of a desensitisation agent, such as those described in U.S. Pat. No. 4,385,008 (Hignett, assigned to Interox Chemicals Limited), a technique that is now so well-known for desensitising other peroxycompounds such as diacyl peroxides and other peroxyacids to those skilled in the art that further description is un-necessary. Compounds outside the range for $R^a$ have been tested also and been found to suffer from increasingly impaired thermal stability and wash performance as the group increases in length through hexyl to octyl.

In general formula (2), the alkylene group $R^b$ is preferably linear, particularly preferred groups being tetramethylene, pentamethylene and hexamethylene. By so choosing the group in accordance with the invention limits and especially for the particularly preferred groups, it is possible to obtain peroxyacids that are not only safe against explosion, as measured by both the impact sensitivity test and the pressure-time tests, but also demonstrate good thermal stability and good wash performance. The substituent X on the benzene nucleus is advantageously para to the amido-peroxy group. X can represent a halogen, typically chlorine, atom, or some other non-released non-interfering species such as a low weight alkyl such as methyl to propyl.

The peroxyacids of the present invention can be made using a strong acid-catalysed reaction between hydrogen peroxide and the corresponding compound containing a carboxylic acid group in the same structural relationship to the amido group as is desired in the peroxycarboxylic acid compound, and preferably employing conditions that have hitherto been described for the peroxidation of other aromatic carboxylic acids or preparation of poorly soluble higher molecular weight aliphatic peroxyacids from their corresponding carboxylic acid. In effect, the teaching in such prior publications as Siegel, et al in JOC, vol 27 pp1336–42 in 1961 entitled peroxides IX. New Method for the Direct Preparation of Aromatic and Aliphatic Peroxyacids can be employed, but modified as to the carboxylic acid starting materials. Thus, the reaction medium for the peroxidation reaction is especially suitably an organic sulphonic acid, such as specifically methane sulphonic acid, which is probably the most readily available lower alkane sulphonic acid. In the case of compounds according to formula (1), the proportion replaced is preferably no more than about 50%, but for compounds according to formula (2), the proportion can comprise 100%, though it is preferable that a small proportion of organic sulphonic acid e.g. 5 to 10%, or more, is retained. It will be understood that where hydrogen peroxide and a strong acid, particularly sulphuric acid are employed in conjunction with each other to carry out the peroxidation reaction, all or part of them can be premixed with each other to form an equilibrium mixture containing for example permonosulphuric acid that can itself perform the peroxidation reaction. Such premixing is beneficial because it separates the exothermic dilution/reaction between hydrogen peroxide and sulphuric acid from the peroxidation reaction, thereby enabling both to be controlled more readily and safely.

The attention of readers not skilled in the art of peroxygen chemistry is directed to the potentially hazardous nature of peroxidation reactions and their products, to the need to take appropriate safety precautions at all times and to control the reaction conditions so as to ensure that the reaction mixture never at any time excedes its SADT, self accelerating decomposition temperature and to carry out any initial tests on a very small scale.

Notwithstanding the above general warning which is of particular relevance to many peroxyacids, the peroxyacids of the instant invention are characterised by their generally benign properties, specifically their relatively high stability and resistance to decomposition which they combine with acceptable bleach performance.

The amido-containing carboxylic acids, if they are not readily available, can themselves be obtained by a conventional condensation between a para or meta amino benzoic acid and the appropriate carboxylic acid anhydride of a monocarboxylic acid for formula (1) compounds and aniline or a substituted aniline with a dicarboxylic acid for formula (2) compounds.

Whilst the instant invention relates primarily to the peroxyacids themselves, it will be understood that it is possible to form magnesium salt derivatives of the peroxyacids by neutralisation using magnesium oxide or similar compounds in media rendered alkaline to above the $pK_a$ of the peroxyacid and recovery of the product that is permitted or induced to precipitate out. These corresponding salts share the stability and performance of the peroxyacids themselves, and accordingly could be employed. However, it will be recognised that it is of benefit for washing and bleaching purposes to avoid the unnecessary introduction of cations that directly contribute to water-hardness, such as magnesium. This particular benefit is inherent in the use of the instant selection of peroxyacids, but is not retained when the corresponding magnesium salt is used. Such magnesium salts tend to enjoy a markedly higher solubility and rate of dissolution than the acid form from which they are derived. Thus, it will be immediately recognised that where it is beneficial to employ a peroxyacid having high water solubility, the user can employ the magnesium salt form of the invention peroxyacids. Where it is desirable to employ peroxyacids having relatively low water solubility, so as to minimise or eliminate bleach spotting problems, the acid form of the invention peroxyacids can be used, preferably. Hereinafter, unless the context clearly demands otherwise, a reference to the use of an invention peroxyacid or compositions containing it includes a reference to use of the corresponding magnesium salt.

The percarboxylic acids according to the instant invention are particulate solids and they can be employed by themselves or can be incorporated as an active bleach component in bleaching or washing compositions containing a range of other ingredients, the selection and amounts of which are at the discretion of the formulator and determine the name for the compositions.

For bleach or bleach additive compositions, the peroxyacid normally comprises from 1 to 80%, and often from 5 to 50%, all %s herein being w/w of the respective composition unless otherwise stated. The remainder, 99 to 20%, comprises a diluent either by itself or together with a minor amount, such as up to 20% in total of optional components such as peroxygen stabilisers, surfactants, etc as indicated subsequently herein. The skilled reader will recognise that many of the diluents described herein as being suitable have hitherto been described as one or other of desensitising diluents or stabilising diluents or exotherm control agents in conjunction with named prior art organic peroxyacids such as DPDDA. Whilst the presence of such diluent compounds may have been necessary to perform that function for those prior art peroxyacids, it is a significant feature of most of the invention peroxyacids that the presence of the same diluents is optional and in practice their selection can be based upon any other desirable feature of those compounds, such as their cheapness or their advantageous washing or detergent-enhancing properties.

The diluent is often a salt selected from anhydrous or hydrated alkali or alkaline earth metal salts of halogen-free acids, and particularly of mineral acids, including salts of sulphuric, and ortho, pyro or hexa-meta phosphoric acids. Preferably, the metal is selected from sodium, potassium and magnesium and in many instances is sodium. Hydrated, partially hydrated or anhydrous sodium sulphate is often chosen in view of its widespread availability, its properties and its cost. It will be recognised, though, that use of a phosphate salt may be preferred in view of its known capabilities of acting as a detergent builder, which can complement especially an unbuilt washing composition.

Other inorganic compounds that are suitable for use as diluents include ortho and meta boric acid and alkali metal salts thereof, and especially sodium salts. Such compounds can buffer solutions of the bleach or additive composition to a pH in the immediate region of the $pK_a$ of the peroxyacid and consequently optimise bleach activity. The boric acids have also been used as exotherm control agents in compositions containing peroxyacids such as DPDDA that need to be protected against a tendency to decompose in an otherwise uncontrollable fashion if allowed to reach a quite low threshold temperature, but that property is unnecessary in conjunction with the invention peroxyacids on account of the safe nature of these selected amidoaryl peroxyacids.

Other suitble inorganic diluents include alkali metal carbonates/bicarbonates, aluminium salts of the above-identified mineral acids, and natural or synthetic aluminosilicates and clays, such as zeolites A, X and Y, often in the sodium form, or swelling clays like bentonite. It will be clearly recognised that many of these diluents also enjoy the status of builders in washing compositions, and that each accordingly can perform its known functions such as hardness removal or peptising when employed in bleach compositions. When the bleach composition is intended as a scour, at least a proportion of the diluent and preferably at least half of the diluent comprises abrasive powdered materials, including silica, quartz, marble dust or kieselguhr.

A further and rather different class of suitable inorganic diluents comprises alkai metal or alkaline earth metal halides, especially chlorides and/or bromides and particularly sodium chloride, or sodium bromide or a mixture of the two. By employing this class of diluents as at least a part of the diluents, the composition can generate in solution during use of the composition a halide such as chlorine or bromine which can complement the bleaching/sanitising effect of the invention amidoaryl peroxyacids.

The diluent can comprise a hydrogen peroxide-developing solid persalts, or an inorganic persulphate, preferably in an amount of not more than 50% w/w of the composition. The term "persalt" herein relates primarily to alkali metal perborates, percarbonates and perphosphates, and especially the sodium salts, which generate hydrogen peroxide or the $HOO^-$ anion depending on the solution pH, in situ and includes other hydrogen peroxide adducts which can do likewise. Preferred persalts include sodium perborate monohydrate or tetrahydrate and sodium percarbonate. Persalts include adducts with urea and related compounds, adducts with certain aluminosilicates and addition compounds with alkali/alkaline earth metal sulphate/chlorides in specified ratios. It will be recognised that the use of persalts as diluent, such as in at least 10% of the composition, enables the composition to be effective throughout a range of temperatures from ambient up to about 100° C.

In one more specialised type of bleaching compositions, namely effervescent composition, which are often intended primarily for cleansing dentures, but which can also be employed for many other purposes, the diluent for the invention peroxyacids preferably contains a gas generating system and if necessary a pH regulator. Compounds that are suitable for gas generating systems and as pH regulators are well known in conjunction with existing peroxyacids, and are described in EP-A-0 133 354 in the name of Interox Chemicals Limited. The gas generating system often provides from 10 to 50% and comprises either a carbon dioxide generating combination of an alkali metal carbonate or bicarbonate with a solid water-soluble acid, and especially an organic acid selected from tartaric, citric, lactic, succinic, glutaric, maleic, fumaric and malonic acids, preferably in an equivalent mole ratio of from 1.5:1 to 1:1.5 and especially at about 1:1, or an oxygen-generating compound such as anhydrous sodium perborate. The pH regulator often comprises 5 to 40% of the composition. To provide acidic conditions, it can comprise one or more of the aforementioned organic acids in an appropriate excess amount, or sulphamic acid or alkali metal bisulphates, and to provide alkaline conditions, it can comprise alkali metal silicates or excess carbonate/bicarbonates. Selection of the percarboxylic salt form can be advantageous in such compositions.

In the main, the foregoing diluents have been inorganic. However, the invention peroxyacids can be diluted, if desired, with a range of organic substances, including hydrocarbon waxes, alkyl C1 to C6 esters of aromatic mono or di carboxylic acids, solid starches, gelatines and dextrins.

The bleach compositions can also contain, as indicated before, minor components such as peroxyacid stabilisers. The breadth of compounds suitable for this purpose is well-known in this art. These are often organic chelating compounds that sequester metal ions in solution, particularly most transition metal ions, which would promote decomposition of any peroxygen compounds therein, and many suitable ones being classified in the literature as carboxylic acid, hydroxycarboxylic or aminocarboxylic acid complexing agents or as organic amino- or hydroxypolyphosphonic acid complexing agents, either in acid or soluble salt forms. Representative stabilisers expressed in acid form include picolinic acid, dipicolinic acid, quinolinic acid, gluconic acid, hydroxyethylene di phosphonic acid, and any compound satisfying the general formula:

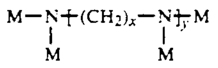

in which M represents either $-CH_2-CO_2H$ or $-CH_2-PO_3H$, x represents an integer selected from 1 to 6, and preferably is 2, and y represents an integer selected from 0, 1, 2 or 3. Within this general formula especially preferred stabilisers include ethylenediamine tetra acetic acid (EDTA), ethylenediamine tetrakis (methylenephosphonic acid) (EDTMP), and diethylenetriamine pentakis (methylenephosphonic acid) (DTPMP). The amount of stabiliser is often up to 5% of the composition and in many instances is selected in the range of from 0.05 to 1%.

If present at all, a surfactant is present in bleaching compositions only in a small amount, such as up to about 5% and in many instances from 0.1 to 2% of the composition. It can be selected from the surfactants described subsequently herein for washing compositions.

The invention bleaching compositions will often comprise particulate mixtures, which can be stored loosely in conventional waxed boxes, or alternatively be enclosed in rupturable pouches or in porous or perforated bags or sacs through which bleaching solution can penetrate. Such mixtures can be obtained by dry blending the particulate components, or they can be aggregated using conventional agglomeration or granulation techniques, using water or a removable solvent and optionally a granulating aid hitherto described for use with an organic peroxyacid. Alternatively, by virtue of their demonstrated ability to withstand pressure, all but the least resistant invention peroxyacids can be compressed in tablets and like bodies. Accordingly, it is possible to provide peroxyacids in easy to use predetermined dosage levels for the end user.

The bleaching compositions can be used by themselves, such as in a pre-wash bleach or a post-wash rinsing stage of a multistage laundry process or in cleansing both absorbent or non-absorbent (sometimes called "hard") surfaces. They are more usually employed in conjunction with a washing composition based upon surfactants. Naturally, surfactants and optional ingredients of washing compositions can be premixed with the instant bleaching compositions to form bleach-containing washing compositions.

Washing compositions according to this further aspect of the present invention contain from 0.5 to 50% of the invention amidoaryl peroxyacids, from 1 to 90% surfactant, from 0 to 90% detergent builder, from 0 to 90% diluent and from 0 to 20% minor components. It will be recognised that the composition of the invention washing compositions range within very broad limits. Choice of the peroxyacid in acid form can be beneficial herein, in order to minimise or avoid spotting problems that can occur if excessive local concentrations of active bleach should be allowed to remain in contact with a dyed fabric for too long.

In many preferred compositions according to the present invention, one or more of the composition components are selected within the following narrower bands:

amidoaryl peroxyacid—1 to 25%, particularly 2 to 10%
surfactant—2 to 40%, particularly 5 to 25%
builder—1 to 60%, particularly 5 to 40%
diluent—1 to 70%, particularly 5 to 50%
minor components—1 to 10% in total.

The surfactants for incorporation in solid compositions of the present invention can be selected from particulate or flaky anionic, cationic, non-ionic, zwitterionic, amphoteric and ampholytic surfactants and can be either natural soaps or synthetic. A number of suitable surfactants are described in chapter 2 of Synthetic Detergents by A. Davidsohn and B. M. Milwidsky (6th edition) published in 1978 by George Godwin Ltd. and John Wiley & Sons, incorporated herein by reference.

Without limiting to the above mentioned surfactants, representative sub-classes of anionic surfactants are carboxylic acid soaps, alkyl aryl sulphonates, olefin sulphonates, linear alkane sulphonates, hydroxy-alkane sulphonates, long chain and OXO alcohol sulphates, sulphated glycerides, sulphated ethers, sulpho-succinates, alkane sulphonates, phosphate esters, sucrose esters and anionic fluorosurfactants; representative classes of cationic surfactants include quaternary ammonium or quaternary pyridinium salts containing at least one hydrophobic alkyl or aralkyl group, representative classes of nonionic surfactants include condensates of a long chain alkanol with either polyethylene oxides or with phenols, or condensates of long chain carboxylic acids or amines or amides with polyethylene oxide, and related compounds in which the long chain moiety is condensed with an aliphatic polypol such as sorbitol or condensation products of ethylene and propylene oxides or fatty acid alkanolamides and fatty acid amine oxides; representative classes of amphoteric/zwitterionic surfactants include sulphonium and phophonium surfactants, optionally substituted by an anionic solubilising group. The proportion of surfactant, expressed as a fraction of all the surfactant present is often from 2/10 to 8/10ths anionic, from 0 to 6/10ths nonionic, and from 0 to 3/10ths for the other surfactants.

It will be recognised by the knowledgable reader that many of the classes of diluent described herein above for use in bleaching compositions are also called detergent builders. These include specifically alkali metal phosphates, particularly tripolyphosphate but also tetrapyrophosphate and hexametaphosphate, especially the sodium salt of each, alkali metal, preferably, sodium carbonate, alkali metal, preferably, sodium borates, and the zeolites A, X and Y and clays like bentonite. Amongst organic compounds, the chelating compounds which were described herein as peroxygen stabilisers can also function as detergent builders. Particularly preferred chelating builders include nitrilotrisodium trisacetate (NTA), EDTA, EDTMP and DTPMP. Such chelating builders can be employed in a relatively small amount as an augmenting builder and peroxygen stabiliser, such as of 1 to 10%, or in cooperative partnership of equals in conjunction with a phosphatic or zeolitic or clay builder, the weight ratio of chelating to inorganic builders often being from 4:1 to 1:4, or alternatively they can be employed as the principal builder in amounts of up to 40% such as in the range of 5 to 30% of the washing composition.

The other types of compounds that have been indicated to be suitable for use as diluents in a bleaching composition, can also be employed for the same primary purpose and secondary purpose, if any, in washing compositions, although it will be recognised that the presence of an effervescent system in washing compositions is comparatively rare. For the avoidance of doubt, persalts can be incorporated in the instant washing compositions, preferably in an amount of up to 30%, such as 1 to 20%, and sometimes in a weight ratio to the invention amidoaryl peroxyacids of from 5:1 to 1:5. A diluent commonly present in these washing compositions is sodium sulphate, often from 5 to 50%, because it also functions as a processing aid. The previously mentioned salts that enable a halogen to be generated in situ can likewise be present in the washing compositions, which can then enjoy the alternative name of sanitising compositions.

The washing compositions can contain a number of optional components, sometimes alternatively called auxiliary agents. These agents which can each individually be included include soil anti redeposition agents (SARDs), dye transfer inhibitors, optical brightening agents (OBAs), stabilisers, corrosion inhibitors, bactericides, dyes, perfumes, foam enhancers, foam inhibitors, pH regulators and absorbents. The amount for each auxiliary agent is often selected in the range of 0.02 to 0.2% for dyes and perfumes and from 0.1 to 2% for each of the other auxiliary agents. It is preferable to select auxiliary agents which are known not to interact with peroxygen compounds during storage or to coat the agent with or incorporate the agent in a known fashion within a matrix of a dispersible material such as a wax or the many other film-forming substances proposed in the literature for separating organic peroxygen compounds from co-components, e.g. in EP-B-00 27 693 to Interox Chemicals Limited. Such substances can also function as granulating aids (binders), if the invention compositions are granulated or agglomerated. Examples of suitable SARDs include carboxymethyl cellulose particularly the sodium salt, polyvinylpyrrolidone and examples of OBAs include derivatives of diaminostilbene sulphonic acid and 1,3-diaryl-2-pyrazolines and aminocoumarins.

The invention washing compositions can be dampened or dissolved in a little water for cleaning and disinfecting non-adsorbent surfaces such as walls, floors, work surfaces, vessels, baths, sinks and sanitaryware of metal, plastics, ceramics or glass, wood and rubber.

One of the main intended uses of the washing compositions is to cleanse and indeed also disinfect soiled adsorbent materials such as household laundry items or other articles made especially from cotton, rayon, flax or wool or man-made fibres such as polyesters or polyamides. The cleansing processes can be carried out at ambient temperature or at elevated temperature up to the boiling temperature of the washing solution. The more preferred washing temperature for laundry is from 30° to 60° C. In laundering, it is desirable to introduce sufficient washing composition and/or bleach additive composition to provide at least 5 ppm avox from the amidoaryl peroxyacid, and often from 10 to 50 ppm avox, ppm indicating parts per million by weight and avox indicating available oxygen. This can often be provided by the introduction of the invention washing composition selected in the range of 1 to 25 gpl, or bleach additive composition selected in the range of from 0.5 to 10 gpl, the selection taking into account the concentration of amidoaryl peroxyacid therein. The presence of persalts in the wash can supplement avox levels, for example by amounts of from 10 to 100 ppm avox. In use, depending upon whether and the extent to which alkaline materials, especially builders, are present in the composition itself or in any accompanying washing composition, the compositions generate upon dissolution either a mildly acidic through to especially a mildly alkaline pH. It is preferred to generate a pH of from 7.5 to 9.5 and especially around pH of 8 to about 9.0 to optimise bleaching/washing performance from the peroxyacid.

For use in disinfection, it is often preferable to employ an invention peroxyacid concentration of up to 200 ppm avox and in many instances from 25 to 100 ppm avox. It is also suitable to employ a solution spanning neutrality, from mildly acidic, such as at least pH 4 up to mildly alkaline, such as pH 9. In order to attain a pH in such a range, the choice of builders/diluents is so made as to avoid highly alkaline materials and instead select those that generate mild acidity or alkaninity such as sodium dihydrogen phosphate.

The washing processes for laundry can be carried out in currently available equipment. Washing times typically range from about 10 minutes to 30 minutes. Hand washing and extended steeping using solutions of the invention compositions can alternatively or additionally be used. Specialist variations of the invention compositions, such as those intended for nappy sanitisation/-cleansing or for denture cleansing are preferably used in the accepted manner for prior art compositions, for example steeping a soiled nappy in a warm peracid-containing solution for several hours before washing it using laundry techniques.

Having described the invention in general terms, specific embodiments will now be described more fully by way of example only.

EXAMPLES 1 TO 5, 8 AND 11 TO 14 AND COMPARISONS C6, C7, C9, C10 AND C14 TO C18.

Preparation of Amidoaryl Peroxyacids.

In each of these Examples and Comparisons, the reaction equation for the acid catalysed reaction was respectively EXAMPLES Ex1 to Ex5, and Ex8 and Comparisons C6, C7

$R^a—CO—NH—C_6H_4—CO—OH+H_2O_2=$-
$R^a—CO—NH—C_6H_4—CO—OOH+H_2O$ or

Comparison C17

$R^a—CO—NH—C_6H_4—CH_2—CO—OH+H_2O_2=$-
$R^a—CO—NH—C_6H_4—CH_2—CO—OOH+H_2O$
or

Comparison C9 and C10 and EXAMPLES Ex11 to Ex 14

$HO—CO—R^b—CO—NH—C_6H_4—X+H_2O_2=$-
$HOO—CO—R^b—CO—NH—C_6H_4—X+H_2O$

Comparisons C15, C16

$HO—CO—R^b—NH—CO—C_6H_5+H_2O_2=$-
$HOO—CO—R^b—NH—CO—C_6H_5+H_2O$

Comparison C18

$HO—CO—R^b—CO—NH—C_8H_{17}+H_2O_2=$-
$HOO—CO—R^b—CO—NH—C_8H_{17}+H_2O$

The general preparative route adopted for the first preparation of each peroxyacid was as follows:

An amidoaryl carboxylic acid (10 g) was introduced into stirred methanesulphonic acid (40 mls) in a beaker, forming a solution or suspension depending upon the solubility of the reactant, and the mixture was cooled to 5° C. in a water/ice bath. Hydrogen peroxide assaying 85% w/w approx. aqueous solution, was pumped via a peristaltic pump with continued stirring into the reaction mixture progressively during a period of about 5 to 10 minutes at a rate controlled so that the mixture's temperature did not rise above 5° C., until a total amount of 4 moles per mole of carboxylic acid had been introduced, i.e. a 3 molar excess compared with the stoichiometric amount. During the subsequent 90 minutes, the reaction mixture was permitted to warm to ambient temperature, i.e. about 20° C. whilst still being stirred. By the end of the reaction a substantial fraction of the carboxylic acid had been oxidised to the corresponding peroxycarboxylic acid, which precipitated out of solution to an extent that varied according to the particular peroxyacid.

The precipitated product was recovered from the reaction mixture by one of a small number of related techniques. In technique A, the reaction mixture was poured into about 3 times as much iced water per volume of reaction mixture, filtered and the filter cake washed twice with about 30 to 40 mls of cool water each time and finally air-dried. In technique B, technique A was followed as far as obtaining the filter cake, and then the latter was extracted into excess dichloromethane, about 500 mls, dried with anhydrous sodium sulphate and the solvent removed on a rotary evaporator.

The isolated peroxyacid product was then analysed by conventional IR and NMR techniques to confirm the presence of amido and percarboxylic acid groups in the product molecule, its available oxygen content measured, again to confirm the presence of a peroxygen species and its "melting" point measured.

The products are summarised in Table 1 below. Position in the Table indicates the relative position of respectively the amidogroup to the percarboxylic acid group in compounds of formula (1) or of substituent X to the amido group in formula (2) around the benzene nucleus. In formula (1), the substituent $R_a$ is named, whereas in formula (2) and in comparisons C15 and C16, the substituent $R_b$ is represented by the integer n in its constituent formula—$(CH_2)_n$—i.e. the number of linear methylene groups. Comparisons C15 and C16, respectively called BurnsP and BurnsH have the same molecular weight and contain the same active groups as P6AN and P7AN in Examples 11 and 12, but the orientation of the amido linking group to the benzene nucleus is reversed, Ar—CO—NH— in C15/C16 and Ar—NH—CO— in Ex 11/Ex 12. C16 is selected for testing because it is the compound named in Example IX of U.S. Pat. No. 4,634,551. C15, which is the adjacent lower member in the homologous series to C16 is selected for testing because the amido group is substituted by the same alkylenepercarboxylic acid group as in Ex 11, $—(CH_2)_4—CO_3H$. Comparison C17 (BurnsD) is selected, because it is the product produced by Burns in Example VI of U.S. Pat. No. 4,634,551 and contains molecular similarities to the products of Ex 1 to C8. Comparison C18 is a further example according to Burns' second formula, but one that is wholly aliphatic, namely N-octyl peroxysuccinamic acid.

The Avox % figure given in Tables 1 and 2, is the percentage obtained by comparing the proportion of peracid avox (available oxygen) measured in the product with the theoretical avox calculated from the molecular formula (16/molecular weight) of the intended peroxycarboxylic acid. The avox was measured by a standard technique in which a measured weight of sample was dissolved in acetic acid, if necessary augmented with dichloromethane to ensure that the sample is completely dissolved. The sample is then contacted with a measured amount of sodium carbonate stabilised sodium iodide, in the presence of ferric chloride, allowed to react for 10 minutes in the dark, and the resultant solution is titrated against standardised sodium thiosulphate solution until the pale yellow coloured solution becomes colourless. The result is compared with a corresponding titration against a blank solution, and from the difference the avox is calculated.

In Tables 1 and 2, a * indicates that the product began to decompose at this temperature rather than simply melting.

TABLE 1

| Ex/Comp | Ref | Substituents Position/$R_a$ | Recovery Method | Yield | Avox % | Melting Point °C. |
|---|---|---|---|---|---|---|
| 1 | 2APB | 4/methyl | A | 70 | 90 | 150* |
| 2 | 3APB | 4/ethyl | A | 94 | 95 | 147* |
| 3 | 4APB | 4/n-propyl | A | 95 | 97 | 150* |

TABLE 1-continued

| Ex/Comp | Ref | Substituents Position/$R_a$ | Recovery Method | Yield | Avox % | Melting Point °C. |
|---|---|---|---|---|---|---|
| 4 | 5APB | 4/n-butyl | A | 93 | 99 | 129* |
| 5 | 6APB | 4/n-pentyl | A | 90 | 86 | 120* |
| C6 | 7APB | 4/n-hexyl | A | 82 | 93 | 105* |
| C7 | 9APB | 4/n-octyl | A | 74 | 92 | 86* |
| 8 | 5mAPB | 3/n-butyl | A | 91 | 99 | 128 |

TABLE 2

| Ex/Comp | Ref | Substituents Position/$R_b$/X | Recovery Method | Yield | Avox % | Melting Point °C. |
|---|---|---|---|---|---|---|
| C9 | P4AN | 4/2/H | A | 72 | 97 | 97 |
| C10 | P5AN | 4/3/H | C | — | 87 | 86 |
| 11 | P6AN | 4/4/H | A | 91 | 95 | 120 |
| 12 | P7AN | 4/5/H | A | 85 | 99 | 103 |
| 13 | P8AN | 4/6/H | A | 95 | 99 | 116 |
| 14 | P6ANX | 4/4/Cl | A | 83 | 96 | 116 |
| C15 | BurnsP | | C | 46 | 82 | <20 |
| C16 | BurnsH | | A | 75 | 100 | 43 |
| C17 | BurnsD | | A | 90 | | 106 |
| C18 | OPSA | | | | 94 | 85 |

The results for Avox % in Tables 1 and 2 are overwhelmingly in the region of 90% or higher, confirming that the product contains one peroxygen group per molecule of starting material, the simplest explanation for which is that the carboxylic acid group has been oxidised to a percarboxylic acid group, as expected.

For each product of Ex 1 through to Ex 14, four significant infra-red peaks were found. The first was in the range of 3300 to 3360 $cm^{-1}$, and this is indicative of N—H stretching in CO—N—H. The second peak was either in the range of 1725 to 1740 $cm^{-1}$ for Ex 1 to Ex 8 or in the range of 1740 to 1765 $cm^{-1}$ for C9 to Ex 14, indicative of carbonyl stretching in a peroxycarboxylic acid which is respectively a direct substituent of an aromatic nucleus or a substituent of an alkylene chain. Thirdly, there were two further peaks, one in the region of 1640 to 1675 $cm^{-1}$, and a second in the region of 1530 to 1545 $cm^{-1}$, which together characterise carbonyl stretching in —CO—NH—. The data for 4APB and P6AN, two representatative sets, comprises significant peaks at 3320, 1735, 1665 and 1540 $cm^{-1}$ for 4APB and at 3360, 1765, 1660 and 1545 $cm^{-1}$ for P6AN. In the corresponding data for the starting materials, the first and third peaks were located in the same regions as in the products and the second peak was located in a range that was displaced lower by approximately 40 $cm^{-1}$, i.e. 1680 to 1700 and 1700 to 1725 $cm^{-1}$ respectively which accords with the known presence of the carboxylic acid substituent in the starting material. By noting the similarities and the extent of the differences in the data, it can be recognised that the products retain the amide group that was present in the starting material and that the carboxylic acid group was oxidised to a peroxycarboxylic acid group.

Most of the products were also analysed by NMR. The products of Ex 1 to Ex 8 were characterised by the presence of three peaks. The first peak was a broad peak at a chemical shift centred in the range of about 171 to 174, which is attributed to the carbon in the amide group. The second peak was a sharp peak centred at a chemical shift of about 165/166, attributed to the carbon in the peroxycarboxylic acid group. The third peak was centred at a chemical shift at about 141/144, attributed to the carbon atom in the benzene nucleus that is substituted by the nitrogen in the amido group. The full spectrum of a representative product, 5APB, which has the formula:

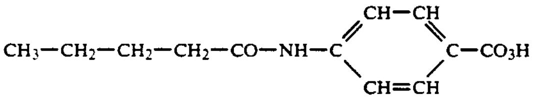

comprised peaks at chemical shifts of 14.4, 22.0, 28.7, 38.5, 118.6, 118.6, 122.4, 127.3, 132.0, 142.3, 165.5 and 176.3. The first four peaks refer to the carbon atoms in the methyl and methylene groups, the next six to the various carbons in the benzene nucleus and the final two to the carbons in the percarboxylic acid and amido groups.

The products of C9 to Ex 14 similarly showed three characteristic peaks, a broad peak for the amido carbon atom, the chemical shift having a centre at about 175/6, between 1 and 5 units above the sharp peak for the percarboxylic acid carbon atom, its chemical shift having a centre at about 171 to 174, and a broad peak for the N-substituted benzene carbon atom, its chemical shift having a centre at 134/140. The full spectrum of the representative product, P6AN, which has the formula:

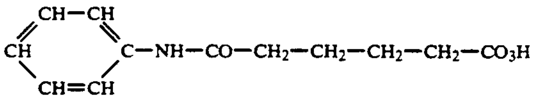

comprised chemical peaks at 24.5, 24.5, 31.7, 36.3, 118.2, 119.1, 123.5, 129.6, 129.6, 140.2, 175.2 and 176.1. The first four peaks are attributed to the four methylene groups, the next five to the unsubstituted carbon atoms in the benzene nucleus and the final three for the N substituted benzene carbon, percarboxylic acid and amido carbon atoms respectively.

It will be recognised that the NMR data confirms the structures implicit from the reaction equations, the avox test and the IR scan.

EXAMPLE 19

Alternative preparation of P6AN

In this Example, a solution of Caro's acid was prepared by mixing sulphuric acid (98% w/w, 20.4 g) and hydrogen peroxide solution (85% w/w, 6.3 g) and demineralised water (5.3 g) with cooling to 20° C., thereby obtaining an equilibrium mixture. Adipanilic acid (10 g) was then introduced, resulting after 10 minutes stirring in a thick white slurry which was stirred, still at ambient temperature, for a further 90 minutes. The reaction mixture was then quenched with ice (100 g), and filtered. The white precipitate was washed with cold water (3×100 ml) allowed to dry and then analysed. The yield of product was 91% based on the adipanilic acid added, having a purity, determined by avox of 90%.

Testing of the peroxyacids

The peroxyacids were subjected to a number of tests to determine their effectiveness as a bleach, their hazard rating and their storage stability. The compounds were also compared in these tests with a reference peroxyacid, diperoxydodecanedioc acid, DPDDA, a peroxyacid that has emerged during the last eight years as a favourite organic peroxide amongst washing composition manufacturers like Procter & Gamble.

The tests were carried out as follows:

Storage stability

In this test, weighed samples of the peroxyacid are individually sealed in glass phials with a bubbler cap that permits excess internal pressure to vent to atmosphere, and stored in a dark chamber that is thermostatically controlled to 32° C. The avox of the peroxyacid is measured shortly after its preparation i.e. $A_0$ and after predetermined storage intervals, $A_s$, the measurement being made on entire individual samples. The stability results of stored samples are $A_s/A_0$, quoted as a percentage, the higher the better.

Avox is measured using the same method as described for Tables 1 and 2.

It will be recognised that the storage stability of the peroxyacid by itself is an extremely important characteristic of a peroxyacid, not only because the compound is likely to be stored in that way before it is encorporated in specific compositions, but also because represents the intrinsic stability of the compound, the maximum attainable even if the remaining components of compositions containing it are benign.

A + indicates in Table 3 that the compound is according to the invention whereas a − indicates that it is present by way of comparison.

TABLE 3

| Compound | Storage Stability<br>Proportion of avox remaining after<br>1 week | 4 weeks | longest/n weeks |
|---|---|---|---|
| +2APB | 100 | 100 | 100/28 w |
| +3APB | 100 | 100 | 98/28 w |
| +4APB | 99 | 100 | 97/14 w |
| +5APB | 96 | 87 | 77/12 w |
| +6APB | 100 | 97 | |
| −7APB | 99 | 89 | 63/8 w |
| −8APB | | 90 | 28/24 w |
| +5mAPB | 98 | 100 | |
| −P4AN | | 19 | |
| −P5AN | 89 | 25 | |
| +P6AN | 98 | 90 | 86/16 w |
| +P7AN | 94 | 92 | 76/16 w |
| +P8AN | 97 | 90 | 85/16 w |
| +P6ANX | 100 | 89 | 83/16 w |
| −BurnsP | 75 (1 day) | | |
| −BurnsH | 37 | 17 (2 weeks) | |
| −BurnsD | 97 | 81 | |
| −OPSA | 15 | 6 (2 weeks) | |
| −DPDDA | 97 | 85 | |

From Table 2, it can be seen that all the alkylamidoperoxybenzoicacids according to formula (1), i.e. in the series APB demonstrated inherent storage stability that range from good to excellent. Specifically, the storage stability of the peroxyacid improved as the number of carbon atoms in the alkyl group decreased. The most storage stable compounds were peroxybenzoic acids sustituted in the 4 position by an ethanamido-, n-propanamido- or n-butanamido-, substituent, which had hardly decomposed at all after three months storage, 3% loss or less, a truly outstanding performance. The corresponding n-pentanamido- and n-hexanamido-compounds also demonstrated very good stability, and even those peroxycompounds outside the instant selection, namely n-heptanamido- and n-nonanamidoperoxybenzoic acids showed stability that is no worse than many organic peroxyacids.

It can also be seen from Table 2 that the storage stability of peroxyacids that obey formula (2) i.e. PnAN compounds ranges from the unacceptable at low alkylene chain lengths to the acceptable at longer alkylene chain lengths. Specifically, the comparison peroxyacid derived from succinanilic acid, P4AN, decomposed to the extent of over 80% in 4 weeks, and P5AN was not much better, whereas the selected invention peroxyacids, P6AN through to P8AN all enjoyed viably good stability, decompositing by only 10% or so in the same period.

The substantial improvement in peroxyacid stability which is made by substituting the benzene nucleus directly by the nitrogen atom of an amido linkage instead of via its carbonyl carbon atom, i.e. Ph—N—CO— instead of Ph—CO—N— can be seen by comparing the stabilities of comparison product P6AN with BurnsP and invention product P7AN with BurnsH. Each of the pairs of peroxyacid have the same molecular weight and structure with the sole exception of which atom in the amido linkage directly substitutes the benzene nucleus. BurnsP had decomposed 25% in its first day, strictly speaking overnight from its preparation one afternoon to its testing the next morning, whereas P6AN decomposed only 14% after 16 weeks. BurnsH, which is a compound that Burns did not make, but is the corresponding compound made by substituting an amino-heptanoic acid instead of amino-caproic acid as his starting material, is better than BurnsP, but still decomposes to the extent of 83% in 2 weeks. On the other hand, P7AN decomposed to the extent of only 24% in 16 weeks, i.e. about 30 times more slowly.

The poor stability result obtained using comparison C18, OPSA, is also very significant. This product, like Burns 4 and BurnsH, is one that is encompassed within Burns' general formulae A or B. Since this is a third result which is contrary to his assertion made in column 2 of lines 39 et seq of U.S. Pat. No. 4,634,551 that his invention peroxyacids show improved thermal stability, it would appear that the assertion is not applicable indescriminately to the general formulae and that accordingly his claims would appear to have been drawn excessively broadly on the basis of Burns' single Example XI and an assumption that the rest of the compounds obeying his general formula have similar stability.

Hazard Rating

Two tests are described below to demonstrate the hazard rating of the peroxyacid. They are respectively an impact sensitivity test and a pressure-time test.

In the impact sensitivity test, a weight (in kg) is dropped once from a measured height (in cm) onto a fresh sample of the peroxyacid held in the anvil. The sample is thus subjected to an impact, normally expressed as kg-cm (1 kg-cm $=9.8\times10^{-2}$J) that is proportionate to the height and weight. The test is carried out many times at each impact strength, and is observed to see whether the sample responds, by charring, emitting smoke or at worst undergoing a minor explosion. The tests start at a low impact strength and are continued at increasing strenghts until the limiting result is obtained, being the earlier of either 50% of the tests at that impact strength give positive results or a figure of 500 kg-cm is reached, which past experience indicates to represent a non-impact-sensitive product. The limiting result in kg-cm is shown in Tables summarising the results, the higher the better.

In the pressure-time test, 2 g samples of the test material is placed inside an 18 ml steel bomb, and its decomposition initiated. The consequential rise in pressure is monitored and plotted or displayed against elapsed time, expressed in milliseconds. In Table 4, the time is given for the pressure in the bomb generated by the sample to increase from 100 to 300 psi, i.e. from $6.895\times10^5$ Pa to $2.068\times10^6$ Pa, the longer the better. The symbol oo indicates that a pressure of 300 psi was not reached, i.e. a period of infinite duration. By way of interpretation, a time of less than 30 milliseconds indicates that the material is potentially explosive, a time of 30 to 60 milliseconds indicates that it is marginally explosive, and to allow a safety margin, it is preferred to be around 100 milliseconds or longer.

TABLE 4

| | Hazards rating results | |
|---|---|---|
| Compound | Impact kg-cm | p-t msec |
| +2APB | 75 | 96 |
| +3APB | >500 | 100 |
| +4APB | 275 | oo |
| +5APB | >500 | oo |
| +6APB | >500 | oo |
| −7APB | >500 | oo |
| −8APB | >500 | oo |
| +5mAPB | >500 | 360 |
| −P4AN | 350 | 130 |
| −P5AN | >500 | oo |
| +P6AN | >500 | oo |
| +P7AN | >500 | oo |
| +P8AN | >500 | oo |
| +P6ANX | >500 | oo |
| −BurnsP | — liquid | — |
| −BurnsH | >500 | oo |
| −BurnsD | >500 | oo |
| −DPDDA | >500 | 30 |

From Table 4, it can be seen that the invention amidoperoxyacids, with a single exception, 2APB, attain an indisputably safe limiting value in the impact test, and in the pressure-time test, all of them, even in the acid form, are significantly safer than the reference compound DPDDA. Bleach/washing evaluation.

The effectiveness of the invention and comparison peroxyacids was tested by washing swatches of cotton cloth that had been preimpregnated in a standard manner with one of four representative stains, tea, red wine, grass and blue polish. The evaluations were carried out in a laboratory scale washing machine, a "Tergotometer" (Trade Mark) available from the U.S. Testing Corporation, under identical standardised conditions. The washing solution comprised local Cheshire tap water, hardness of about 160 to 180 ppm hardness as calcium carbonate, in which was dissolved a peroxyacid-free washing composition at 6.5 g/l. Composition DB1 was used in all trials except C33 to C35, which employed composition DB2. The compositions had the approximate composition analyses:

| Composition Component | DB1 % w/w | DB2 % w/w |
|---|---|---|
| Anionic surfactant | 10 | 9 |
| Nonionic surfactant | 4 | 6 |
| Other organics | 4 | 17 |
| Sodium carbonate | 1 | <1 |
| Sodium sulphate | 40 | 25 |
| Sodium phosphate | 27 | <1 |
| Sodium silicate | 7 | 8 |
| Zeolite A | | 23 |
| Water | 7 | 10 |

A weighed amount of peroxyacid was introduced into the washing solution to provide a peracid avox of 25 ppm therein, assuming total dissolution. This corresponds to a molar concentration of $1.56\times10^{-3}$M monoperoxyacid. The washing solution was kept at pH9 and at 40° C. during the washing period of 20 minutes. The swatches were then rinsed and dried and the extent of stain removal was determined by comparing the reflectance of the washed cloth, $R_w$, with that of the pre-washed, stained cloth, $R_s$, and that of the unstained cloth, $R_u$. The measurements were obtained using an Instrumental Colour System "Micromatch" (Trade Mark) reflectance spectrophotomer equipped with a Xenon lamp filtered through a D65 conversion filter to approximate to CIE artificial daylight. Stain Removal, expressed a s percentage, was calculated using the formula:

$$\%SR=100\times[R_w-R_s]/[R_u-R_s]$$

It will be recognised that by demonstrating the washing capability of the peroxyacids in this way, the tests using the invention peroxyacids are in themselves Examples of washing processes according to other aspects of the present invention. Similarly, since the swatches had not been stored in sterile conditions before being washed, the washing procedure will act simultaneously to disinfect them.

The results quoted below are the mean of two evaluations. Comparative results on the same stained cloths using the washing composition by itself, i.e. without any added peracid, are designated "base".

TABLE 5

| | | % Stain Removal | | | | |
|---|---|---|---|---|---|---|
| Ex/Comp No | Peracid employed | Red Wine | Grass | Tea | Blue Polish | Average Removal |
| C20 | base | 63 | 48 | 67 | 35 | 53 |
| 21 | 2APB | 83 | 65 | 90 | 44 | 71 |

TABLE 5-continued

| Ex/Comp No | Peracid employed | % Stain Removal | | | | |
|---|---|---|---|---|---|---|
| | | Red Wine | Grass | Tea | Blue Polish | Average Removal |
| 22 | 3APB | 85 | 69 | 92 | 46 | 73 |
| 23 | 5APB | 86 | 70 | 90 | 48 | 74 |
| C24 | 9APB | 77 | 62 | 79 | 46 | 66 |
| C25 | DPDDA | 80 | 64 | 86 | 44 | 69 |
| C26 | base | 34 | 47 | 65 | 39 | 46 |
| 27 | 3APB | 70 | 66 | 89 | 40 | 66 |
| 28 | 4APB | 69 | 65 | 89 | 39 | 66 |
| 29 | 5APB | 72 | 67 | 88 | 41 | 67 |
| 30 | 6APB | 68 | 67 | 85 | 47 | 67 |
| 31 | 5mAPB | 72 | 66 | 88 | 46 | 68 |
| C32 | DPDDA | 63 | 63 | 85 | 47 | 65 |
| C33 | base | 42 | 57 | 17 | 38 | 39 |
| C34 | BurnsD | 48 | 69 | 35 | 55 | 52 |
| C35 | DPDDA | 63 | 75 | 44 | 47 | 57 |
| C36 | base | 35 | 52 | 70 | 37 | 49 |
| 37 | P6AN | 70 | 69 | 88 | 39 | 67 |
| 38 | P7AN | 69 | 70 | 87 | 46 | 68 |
| 39 | P8AN | 69 | 71 | 88 | 50 | 70 |
| 40 | P6ANX | 68 | 72 | 86 | 45 | 68 |
| C41 | DPDDA | 66 | 70 | 85 | 46 | 67 |
| C42 | base | 62 | 46 | 64 | 44 | 54 |
| C43 | P4AN | 66 | 49 | 69 | 47 | 58 |
| C44 | P5AN | 75 | 58 | 82 | 46 | 65 |
| 45 | P6AN | 81 | 64 | 88 | 36 | 67 |

From Table 5, it can be seen that all the invention peracids are very effective bleaching agents at hand-hot washing temperatures, by comparing the stain removal obtained in the presence and absence of the peroxyacid and also noting that their performance matches or excedes that of a well-established peroxyacid, DPDDA. The first and second blocks of results show that amidoperacids obeying formula (1) herein, i.e. in the nAPB series, show excellent washing performance within the invention range, 2APB to 6APB. The performance of even the higher molecular weight compounds of 7APB and higher is still very good, and similar to or nearly as good as DPDDA, and such compounds would be very useful if they could be adequately stabilised against decomposition during storage. The fourth and fifth block of results show that invention peracids obeying formula (2) are very good or excellent bleaching agents in hand-hot washing temperatures, but that the low molecular weight members of the PnAN series which are not according to the invention show significantly inferior bleaching activity.

A second series of trials was conducted in the Tergotometer washing machine using the same set of washing conditions as in preceding Ex21, but employing a wash pH maintained at pH 8.5 and the range of washing temperatures specified in Table 6 below. The result for stain removal given in Table 6 is an average of three differently stained cotton swatches; red wine, grass and tea.

TABLE 6

| Example/ Comparison | Bleaching Agent | Average % Stain Removal at °C. | | | |
|---|---|---|---|---|---|
| | | 20 a | 40 b | 60 c | 80 d |
| C46 a-d | base | 46 | 58 | 69 | 80 |
| 47 a-d | 4APB | 62 | 81 | 87 | 86 |
| 48 a-d | 5APB | 67 | 82 | 87 | 89 |
| 49 a-d | P6AN | 66 | 78 | 83 | 86 |

The results for the second series of trials show that the invention peroxyacids significantly improve the stain removal at 20° C., 40° C. and 60° C. and continue to cause some improvement in stain removal at 80° C., confirming that the most benefit from the peroxyacids can be enjoyed at washing temperatures in the range of from ambient to about 70° C.

A third series of trials was conducted in the Tergotometer washing machine and using the same procedure as in the second series of trials, but always at a wash temperature of 40° C., and employing the concentration of the bleaching agent in the washing liquor specified in Table 7 below. For ease of comparison, the concentration quoted is the amount of the Avox introduced into the washing liquor.

TABLE 7

| Example/ Comparison | Bleaching Agent | Average % Stain Removal at Avox of | | |
|---|---|---|---|---|
| | | 5 ppm a | 25 ppm b | 50 ppm c |
| C50 a-c | base | 58 | 58 | 59 |
| 51 a-c | 4APB | 67 | 81 | 81 |
| 52 a-c | 5APB | 69 | 82 | 83 |
| 53 a-c | P6AN | 67 | 78 | 82 |

The results obtained in the third series of trials demonstrate very clearly that a noticeable improvement in stain removal is obtained using peroxyacid concentrations of the invention peroxyacids of as little as 5 ppm avox, $3.12\times10^{-4}$M peroxyacid. The results also show that the benefit is extremely apparent at invention peroxyacid concentrations providing about 25 ppm avox, and is little changed when the concentration is increased to about 50 ppm avox.

A fourth series of trials was conducted in the Tergotometer washing machine using the same procedure as in the second series of trials, but always at 40° C. washing temperature and maintaining the liquor at the pH specified in Table 8 below.

TABLE 8

| Example/ Comparison | Bleaching Agent | Average % Stain Removal at | |
|---|---|---|---|
| | | pH 8.5 a | pH 10.5 m b |
| C54 a-b | base | 57 | 47 |
| 55 a-b | 4APB | 81 | 61 |
| 56 a-b | 5APB | 82 | 66 |
| 57 a-b | P6AN | 78 | 63 |

The results in the fourth series of trials confirm that stain removal is much better at a solution pH of 8.5 which is close to the $pK_a$ of peroxyacids compared with using a significantly higher solution pH of 10.5. When the results in Table 5 are also taken into account, they show that a pH range from about pH 8.5 to about pH 9 is very effective.

A fifth series of washing trials was carried out in a Philips AWB 098 domestic washing machine, using its 40° C. main wash cold fill cycle and employing swatches of prestained cotton and polyester/cotton blend in a bulk load of white cotton. The range of swatches comprised cotton stained with red wine, grass, tea, coffee, "Spangler", "EMPA" 101 and blue polish and Cotton/polyester blend stained with red wine, grass, tea, "Spangler" and "EMPA" 101. In each wash, the total amount of detergent base (the same as in the preceding trials) and any bleaching agent was 200 g, and the weight of bleaching agent used was adjusted to provide an avox concentration of 25 ppm. The bleaching agent in C59 was sodium perborate monohydrate. The water was local Cheshire tap water. The extent of stain removal was measured in the same way as for the preceding washing trials. The trials were repeated and the mean stain removal was employed to assess the effectiveness of the washing formulations, which are expressed in the Table 6 below as an average calculated from the results obtained for each of the various stains for each fabric.

TABLE 9

| Example/ Comparison | Bleaching Agent | Average % Stain Removal Cotton | Polyester/Cotton |
|---|---|---|---|
| C58 c,p | base | 47 | 62 |
| C59 c,p | PBS1 | 55 | 69 |
| 60 c,p | P6AN | 71 | 82 |
| C61 c,p | DPDDA | 67 | 75 |

The results given in Table 9 using the domestic washing machine confirm the reliability of the small-scale trials in the Tergotometer. Once again, these results show that addition of the invention peroxyacid to provide only 25 ppm avox very significantly improves the stain removal, not only from cotton materials but also from cotton/polyester blends. Moreover, the improvement is demonstrated over a substantially wider range of stains than in the small-scale trials. The trials additionally show that the invention peroxyacid is a much better bleach than a hydrogen peroxide-developing compound, PBS1 and demonstrates more clearly than the small scale trials that the peroxyacid is better than the known DPDDA.

Bleach Additive Formulations

Representative formulations are made by dry mixing particulate invention peroxyacid with a premixture of the remaining components. The peracids have the names given in Tables 1 and 2. LAS represents a linear alkyl benzene sulphonate, sodium salt, average alkyl length of C11.5, and OBA represents an optical brightening agent.

TABLE 10

| Example No Particulate Components | 62 % w/w | 63 % w/w | 64 % w/w |
|---|---|---|---|
| 4APB (6.9% avox) | 6 | | |
| 5APB (6.7% avox) | | 24 | |
| P6AN (6.4% avox) | | | 50 |
| LAS | 3 | 4 | 5 |
| OBA + chelate | 0.2 | 0.2 | 0.2 |
| Sodium sulphate | 90.8 | 71.8 | 44.8 |

Dosing of formulations 61, 63 and 64 each at 1.25 gpl provides respectively avox concentrations in solution of approximately 5 ppm, 20 ppm and 40 ppm. Corresponding formulations employing the other two of 4APB, 5APB and P6AN are obtained by substituting the corresponding weight of peroxyacid for the weight given above, based on its relative avox, and adjusting the sodium sulphate balance correspondingly. For example, when employing 4APB in composition 64 instead of P6AN, the peracid content is reduced to 46.4% and the sulphate content increased to 48.4%. Solid bleach additive compositions containing a pH buffer to lower the solution pH closer to about pH 8.5, and hence improve stain removal are made by replacing about 10% w/w of the sodium sulphate by boric acid.

Washing Formulations

Representative washing compositions according to the present invention are made by dry mixing the particulate invention peroxyacid with a blend of the other components shown in Table 11. The abbreviations STPP and PBS1 represent respectively sodium tripolyphosphate and sodium perborate monohydrate. The chelating agent is EDTMP, ethylene diamino (tetramethylene phosphonate), Na salt.

TABLE 11

| Example No Components | 65 % w/w | 66 % w/w | 67 % w/w | 68 % w/w | 69 % w/w | 70 % w/w |
|---|---|---|---|---|---|---|
| 4APB (6.9% avox) | | | 5.4 | 2.7 | | |
| 5APB (6.7% avox) | | 3.7 | | | 4.7 | |
| P6AN (6.4% avox) | 2.0 | | | | | 6.9 |
| LAS | 7.0 | 9.6 | 8.6 | 7.0 | 6.0 | 6.0 |
| Alcohol Ethoxylate | 5.1 | 3.8 | 5.7 | 2.5 | 6.0 | 7.0 |
| STPP | 34.0 | 26.1 | | 40.0 | 30.0 | 30.0 |
| Zeolite A | | | 22.5 | | | |
| Carboxylate builder | | 2.0 | 15.0 | | | |
| Sodium sulphate | 14.0 | 38.5 | 24.0 | 18.5 | 23.5 | 16.0 |
| Sodium silicate | 14.0 | 6.7 | 7.6 | 6.5 | 5.0 | 5.0 |
| Soap | 6.5 | | | 3.0 | 3.0 | 2.0 |
| Buffer (boric acid) | 10.0 | | | 10.0 | 10.0 | 10.0 |
| PBS1 | | | | | | 9.0 |
| CMC | 1.0 | 1.0 | 1.0 | 1.0 | 1.0 | 1.0 |
| Minors (OBA + Perfume + Chelate) | 0.4 | 0.4 | 0.4 | 0.6 | 0.3 | 0.5 |
| Water | | | balance | | | |

Use of example formulations 65 to 70 at a concentration of 8 gpl in the washing liquor, a typical level for front loading washing machines in Europe, results in peracid avox concentrations of respectively 10, 20, 30, 15, 25, and 35 ppm. Similar compositions are made by substituting the other invention peracids made according to a scale-up version of any of Examples 1 to 5, or 8 or 11 to 14 for respectively 4APB, 5APB and P6AN specified in any one composition 65 to 70, and adjusting their content in line with the measured avox in the peroxyacid product. A corresponding and balancing adjustment to the content of either the inorganic diluent, sodium sulphate and/or to the inorganic builder, STPP or zeolite is also made.

Sanitizer formulations

Representative formulations are made by dry mixing the specified invention peroxyacids with the other components specified in Table 12.

TABLE 12

| Example No Particulate Components | 71 % w/w | 72 % w/w | 73 % w/w |
|---|---|---|---|
| 4APB (6.9% avox) | | | 10.2 |
| 5APB (6.7% avox) | 4.5 | | |
| P6AN (6.4% avox) | | 7.8 | |
| LAS | 9.0 | 7.0 | 5.0 |
| Sodium carbonate | 20.0 | 23.0 | |
| STPP | 10.0 | 10.0 | 10.0 |

TABLE 12-continued

| Example No Particulate Components | 71 % w/w | 72 % w/w | 73 % w/w |
|---|---|---|---|
| Sodium bicarbonate | | | 26.0 |
| Sodium chloride | 48.0 | 51.0 | 48.0 |
| Borax | 8.5 | | |
| Organic chelate | | 1.2 | 0.8 |

When these formulations are dosed into a nappy (or similar article) sanitising solution in an amount of 5 gpl, the invention peroxyacids provide an avox of respectively 35, 15 and 25 ppm approximately in Compositions 71, 72 and 73. Compositions of similar efficacy are made by substituting invention peracids made according to a scale-up version of any of Examples 1 to 5, or 8 or 11 to 14 for respectively 4APB, 5APB and P6AN specified in any one composition 71, 72 or 73.

Dilute disinfectant compositions

Particulate disinfectant compositions are made by dry mixing the components specified in Table 13.

TABLE 13

| Example No Particulate Components | 74 % w/w | 75 % w/w | 76 % w/w |
|---|---|---|---|
| 4APB (6.9% avox) | 4.3 | | |
| P5AN (6.7% avox) | | 7.5 | |
| P6AN (6.4% avox) | | | 10.9 |
| Sodium dihydrogen phosphate | 10.0 | 10.0 | 10.0 |
| Boric acid | 5.0 | 5.0 | 5.0 |
| Corrosion Inhibitor | 1.0 | 1.0 | 1.0 |
| Perfume | 0.5 | 0.5 | 0.5 |
| Sodium sulphate | 79.2 | 76.0 | 72.6 |

When these formulations are employed at a dose level of 1 glp in an aqueous medium requiring disinfection, the concentration of avox therein is respectively 3, 5 and 7 ppm from compositions 74, 75 and 76. Similar compositions are made by substituting invention peracids made according to a scale-up version of any of Examples 1 to 5, or 8 or 11 to 14 for respectively 4APB, 5APB and P6AN specified in any one composition 74, 75 or 76.

Disintegrating Tablet compositions—suitable for dentures

Representative compositions of this type are made by dry mixing the components given in Table 14 below, and then subjecting them to compression in the mould of a tabletting machine to make tablet weighing about 4 g. The polyethyleneglycol binder av mol weight 6000 is designated PEG 6000, the disintegrant was a cross linked polyvinylpyrrolidone available under the Trademark POLYPLASDONE XL and the lubricant was sodium lauryl sulphate.

TABLE 14

| Example No Particulate Components | 77 % w/w | 78 % w/w | 79 % w/w |
|---|---|---|---|
| 4APB (6.9% avox) | 6.0 | | |
| P5AN (6.7% avox) | | 8.0 | |
| P6AN (6.4% avox) | | | 10.0 |
| Succinic acid | 25.0 | 15.0 | 15.0 |
| Sodium Bicarbonate | | 25.0 | 40.0 |
| Sodium Carbonate | 10.0 | | |
| PEG 6000 (binder) | 6.0 | 6.0 | 6.0 |
| PVP disintegrant | 1.0 | 1.0 | 1.0 |
| Lubricant | 0.2 | 0.2 | 0.2 |
| Sodium sulphate | 51.8 | 44.8 | 27.8 |

When one tablet of tablet 77, 78 or 79 is introduced into water it generates respectively 17, 21.5 or 25.6 mg avox. Similar tablet compositions are made by substituting invention peracids made according to a scale-up version of any of Examples 1 to 5, or 8 or 11 to 14 for respectively 4APB, 5APB and P6AN specified in any composition 77, 78 or 79.

We claim:

1. An organic peroxyacid which satisfies one or other of the general formulae (1) or (2):

$$R^a—CO—NH—C_6H_4—CO—OOH \quad (1) \text{ or}$$

$$HOO—CO—R^b—CO—NH—C_6H_4—X \quad (2)$$

in which in formula (1) the amido substituent is meta or para to the percarboxylic acid group and $R^a$ represents an alkyl group containing from 1 to 5 carbons in formula (1) and in formula (2) $R^b$ represents a linear or branched alkylene group containing from 4 to 7 carbon atoms of which at least 4 are linear and X represents hydrogen or a compatible non-released substituent.

2. A peroxyacid according to claim 1 which satisfies formula (1) and in which $R^a$ represents a linear alkyl group containing from 2 to 4 carbon atoms.

3. A peroxyacid according to claim 1 which satisfies formula (2) and in which $R^b$ represents a linear alkylene group containing 4 or 5 carbon atoms.

4. A method of bleaching or disinfecting an article which comprises contacting an article with an aqueous bleaching or disinfecting solution comprising a peroxy acid according to claim 1.

5. A method of washing an article which comprises contacting an article with an aqueous washing solution comprising a surfactant, a detergent builder, and a peroxy acid according to claim 1.

* * * * *